United States Patent
Okutsu et al.

(10) Patent No.: US 6,504,063 B2
(45) Date of Patent: Jan. 7, 2003

(54) PROCESS FOR PRODUCTION OF MONOALKYL ETHERS

(75) Inventors: Munehisa Okutsu, Wakayama (JP); Tomohito Kitsuki, Wakayama (JP); Atsushi Nagasawa, Wakayama (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 09/867,460

(22) Filed: May 31, 2001

(65) Prior Publication Data

US 2001/0056212 A1 Dec. 27, 2001

(30) Foreign Application Priority Data

May 31, 2000 (JP) ........................ 2000-161691
Feb. 7, 2001 (JP) ........................ 2001-030618

(51) Int. Cl.$^7$ ............................................. C07C 41/01
(52) U.S. Cl. ...................................................... 568/680
(58) Field of Search ......................................... 568/680

(56) References Cited

U.S. PATENT DOCUMENTS

| 4,006,192 | | 2/1977 | Enomoto et al. |
| 5,100,854 | * | 3/1992 | Maeda et al. ............... 502/164 |

FOREIGN PATENT DOCUMENTS

| DE | 40 21 478 | | 1/1992 | |
| FR | 2 693 188 | | 1/1994 | |
| GB | 2114974 | * | 9/1983 | ........... C07C/41/06 |
| WO | WO 90/13531 | | 11/1990 | |
| WO | WO 93/02032 | | 2/1993 | |

OTHER PUBLICATIONS

U. M. Dzhemilev, et al., Journal of Organic Chemistry of the USSR, vol. 16, No. 4, XP–002200695, pp. 999–1002, "Telomerization of Polyhydric Alcohols with Butadiene, Catalyzed by Low–Valence Complexes of Palladium", Apr. 1980.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

A process for producing a monoalkyl ether which comprises a first step of contacting the following components (A) and (B):(A): an aqueous liquid phase containing: ($a_1$) a $C_{3-6}$ polyol having 3 or 4 hydroxyl groups, a palladium compound, a water-soluble tertiary phosphine or phosphite, and water; or ($a_2$) a $C_{3-6}$ polyol having 3 to 4 hydroxyl groups, a complex of palladium and a water-soluble tertiary phosphine or phosphite, and water, and (B): an oily liquid phase containing a conjugated diene, to give an alkadienyl ether containing an alkadienyl group resulting from dimerization of conjugated dienes; and a second step of hydrogenating the alkadienyl group in the alkadienyl ether in a hydrogen atmosphere in the presence of a catalyst containing an element selected from the Groups 8 to 10 elements of the periodic table.

According to the process of the invention, monoalkyl ethers of polyols are produced selectively in a simple manner and advantageously from the economical viewpoint. The present process enables recovery and recycling of the catalyst.

23 Claims, No Drawings

PROCESS FOR PRODUCTION OF MONOALKYL ETHERS

TECHNICAL FIELD

The present invention relates to a process for production of monoalkyl ethers of polyols, particularly monoalkyl glyceryl ethers.

BACKGROUND ART

Monoalkyl ethers of polyols (which may be hereinafter called as "monoalkyl ethers") represented by monoalkyl glyceryl ethers are excellent nonionic surfactants for emulsions, dispersants or detergents.

A production process of monoalkyl glyceryl ethers usually used is (1) a process which comprises synthesizing a glycidyl ether from an alcohol and an epihalohydrin such as epichlorohydrin, followed by hydrolysis. Also known are (2) a process comprising reacting an alkyl halide with glycerin by using a base, (3) a process comprising directly reacting an alcohol and glycerin in the presence of an acid catalyst, and (4) a process comprising reacting an alcohol with glycidol by using an acid or base catalyst.

In the process (1), however, selective synthesis of a glycidyl ether is difficult and in addition, there is a possibility that organic chlorides derived from the raw material may be contaminated. In the process (2), not only selective synthesis of a monoalkyl glyceryl ether is difficult, but also a large amount of salt byproducts must be treated. In addition, the process (2) involves a problem that the products are significantly colored. In the process (3), selective synthesis of a monoalkyl glyceryl ether is difficult. In addition, the process (3) is inevitably accompanied with the problem of by-production of dialkyl glyceryl ethers or dialkyl ethers resulting from an alcohol-alcohol reaction. The process (4) involves the problem that it is difficult to avoid polymerization of glycidol itself or excessive addition of glycidol to the product.

It is known that 1,7- or 2,7-alkadienyl ethers are produced by telomerization of a conjugated diene with an alcohol or polyol. In WO 93/02032 and DE 4021478 A1, there is disclosed a process for synthesizing an alkadienyl glyceryl ether by telomerization of a conjugated diene and a polyol, particularly glycerin, in a solution of a secondary alcohol such as 2-propanol. The resulting alkadienyl glyceryl ether can be then hydrogenated to give an alkyl glyceryl ether. According to this process, however, it is difficult to selectively synthesize a monoalkadienyl glyceryl ether because the alkadienyl glyceryl ethers thus produced by telomerization are changed to a mixture of the monoethers with a diether or a triether. Moreover, it is difficult to recover and reuse the catalyst in this process.

An object of the present invnetion is to provide a process for selectively producing a monoalkyl ether of a polyol, particularly a $C_{3-6}$ polyol having 3 or 4 hydroxyl groups, which process is simple, advantageous from the economical viewpoint, and enables recovery and recycling of the catalyst.

DISCLOSURE OF THE INVENTION

The present invention provides a process for producing a monoalkyl ether, which comprises a first step of contacting the following components (A) and (B):

(A): an aqueous liquid phase containing:
($a_1$) a $C_{3-6}$ polyol having 3 or 4 hydroxyl groups, a palladium compound, a water-soluble tertiary phosphine or phosphite, and water; or
($a_2$) a $C_{3-6}$ polyol having 3 to 4 hydroxyl groups, a complex of palladium and a water-soluble tertiary phosphine or phosphite, and water, and (B): an oily liquid phase containing a conjugated diene to give an alkadienyl ether containing an alkadienyl group resulting from dimerization of conjugated dienes; and a second step of hydrogenating the alkadienyl group in the alkadienyl ether in a hydrogen atmosphere in the presence of a catalyst containing an element selected from the Groups 8 to 10 elements of the periodic table.

BEST MODE FOR CARRYING OUT THE INVENTION

<First Step>

Specific examples of the $C_{3-6}$ polyol having 3 or 4 hydroxyl groups used in the present invention include triols such as glycerin, trimethylolmethane, trimethylolethane and trimethylolpropane, and tetraols such as pentaerythritol. Among them, triols are preferred, and glycerin is particularly preferred. In the aqueous liquid phase used in the first step, the polyol is preferably incorporated in an amount of 0.01 to 10 times, more preferably 0.1 to 10 times, especially 2 to 5 times, the weight of water.

Examples of the palladium compound contained in the aqueous liquid phase include bis(acetylacetonato)-palladium (II), palladium (II) acetate and palladium (II) chloride, of which bis(acetylacetonato)palladium (II) and palladium acetate are preferred. One or two or more of these palladium compounds may be used.

In place of using the palladium compound and water-soluble tertiary phosphine or phosphite, a complex of palladium with a water-soluble tertiary phosphine or phosphite may be used. Preferred examples of such complex include mono-, di-, tri- or higher sulfonated tetrakis (triphenylphosphine)palladium(0) and metal salts thereof. One or two or more of these palladium complexes may be used.

The palladium compound or the palladium complex with water-soluble tertiary phosphine or phosphite is preferably used in an amount of 0.0001 to 0.1 molar time, more preferably 0.001 to 0.1 molar time, especially 0.001 to 0.01 molar time of the polyol.

The water-soluble tertiary phosphine or phosphite to be incorporated, together with a palladium compound, in the aqueous liquid phase, is preferably sulfonated tertiary phosphines or phosphites, or alkali metal salts thereof. Examples thereof include mono-, di- or tri-sulfonated aliphatic (preferably of 1-20 total carbon atoms) phosphines such as trimethylphosphine, and alkali metal salts thereof; mono-, di-, tri- or higher sulfonated aromatic or aromatic-aliphatic (preferably of 8-32 total carbon atoms) phosphines such as triphenylphosphine, dimethylphenylphosphine, methyldiphenylphosphine, diethylphenylphosphine and ethyldiphenylphosphine, and alkali metal salts thereof; mono-, di-, tri-, tetra- or higher sulfonated tertiary phosphines which serve as a bidentate ligand, such as 1,2-bis (diphenylphosphino)ethane, 1,3-bis(diphenylphosphino) propane, 1,4-bis(diphenylphosphino)butane, 1,4-bis (dimethylphosphino)butane and 1,2-bis (dimethylphosphino)ethane, or alkali metal salts thereof; and sulfonated phosphites having a similar structure to the above-described sulfonated phosphines, and alkali metal salts thereof. These tertiary phosphines or phosphites act as a ligand of a part of or the whole of the palladium atoms contained in the palladium compound and can dissolve the part or whole of the palladium compound in the aqueous liquid phase. Alternatively, compounds having a carboxyl group as a substituent for a part or the whole of the sulfonic acid groups contained in the sulfonated phosphine or phosphite are also preferably used. The sulfonic acid group or carboxyl group should be contained in the tertiary phosphine or phosphite in such an amount that allows easy dissolution of the resulting tertiary phosphine or phosphite in water. Among them, preferred are sulfonated aromatic tertiary phosphines or phosphites (including the compounds serving as a bidentate ligand), and alkali metal salts thereof such as, for example, triphenylphosphine trisulfonic acid and trisodium salt thereof, and triphenylphosphine disulfonic acid and dipotassium salt thereof.

The water-soluble tertiary phosphine or phosphite is used preferably in an amount of 0.1 to 4 molar times, especially 1 to 4 molar times of the palladium compound when the tertiary phosphine or phosphite is used in a sulfonated form (or carboxylated form) or its alkali metal salt is used. A tertiary phosphine or phosphite serving as a bidentate ligand, on the other hand, is preferably used in an amount of 0.1 to 2 molar times, especially 0.5 to 2 molar times of the palladium compound.

As the conjugated diene contained in the oily liquid phase, 1,3-alkadienes and 2,4-alkadienes can be mentioned, and alkadienes of 4-6 carbon atoms, particularly 1,3-alkadienes of 4-6 carbon atoms are preferred. Specific examples thereof include 1,3-butadiene, 1,3-pentadiene, 1,3-hexadiene and isoprene. Of these, 1,3-butadiene is especially preferred. By using 1,3-butadiene, it is possible to produce monooctyl glyceryl ether and other monooctyl ethers of polyols, all of which ethers exhibit an excellent performance as a nonionic surfactant.

The monoalkyl ethers of a polyol produced according to the present invention are mono($C_{8-12}$ alkyl) ethers of a polyol corresponding to the $C_{4-6}$ alkadienes used as a conjugated diene. The alkoxy group of the monoalkyl ether may be bonded to a hydroxyl group at any position of the polyol, but usually it is preferentially bonded to a primary hydroxyl group of the polyol.

As a solvent for the oily liquid phase of the present invention, it is preferred to use the conjugated diene which is also used for the reaction, but other solvents may be used, as necessary. As the other solvents, a solvent which can dissolve both the conjugated diene used in the reaction and resulting alkadienyl ethers, and is immiscible with the aqueous liquid phase is preferred. Hydrocarbon solvents and glycol diethers are preferred as the solvent.

Particularly when a polyol other than glycerin is employed, use of a glycol diether is preferred in view of control of the reaction.

Examples of the hydrocarbon solvent include $C_{6-20}$ saturated aliphatic hydrocarbons such as hexane, heptane, octane, nonane, decane, undecane, dodecane, tridecane, tetradecane, pentadecane, hexadecane, heptadecane, octadecane, nonadecane and icosane. Use of the conjugated diene which is used as a reactant is also preferred as the solvent.

The glycol diethers, when used as a solvent, preferably have total carbon atoms of 20 or less. Specific preferred examples include glycol diethers such as ethyleneglycol dialkyl ethers and diethyleneglycol dialkyl ethers. Ethyleneglycol dibutyl ether, ethyleneglycol butyl methyl ether, ethyleneglycol butyl ethyl ether and diethyleneglycol dibutyl ether are more preferred.

The hydrocarbon solvent phase containing a conjugated diene may be charged at one time or introduced continuously to a reaction vessel such as autoclave. It is preferred to introduce the hydrocarbon solvent phase into the vessel in such a manner that the conjugated diene amounts to 1.0 to 10.0 molar times, especially 1.0 to 6.0 molar times of the polyol in the aqueous liquid phase.

In the first step, the reaction temperature is preferably kept at 10 to 100° C., especially at 60 to 100° C.

Since a larger portion of the catalyst exists in the aqueous liquid phase in the first step, it is possible to recover the aqueous liquid phase containing the catalyst and unreacted polyol in a conventional manner after the reaction, and then add thereto a necessary amount of the polyol to provide an aqueous liquid phase to be used for the reaction.

<Second step>

The catalysts, containing an element selected from the Group 8 to 10 elements and used for hydrogenation of the alkadienyl group in the second step, include those catalysts that contain a metal selected from Fe, Co, Ni, Ru, Rh, Pd, Os, Ir and Pt, preferably a metal such as Pd, Rh, Ru, Ni or Pt that is contained in a low oxidation state. Catalysts having 1 to 10 wt. % of such metal carried on carbon, zeolite or silica alumina; Raney nickel; and oxides of such metals are preferred. The catalyst is preferably used in an amount of 0.1 to 10 wt. % based on the amount of the alkadienyl ether product. Although no particular limitation is imposed on the hydrogen pressure, a range of from normal pressure to 20 MPa is preferred.

EXAMPLES

Example 1

In a 500-mL autoclave, charged were 70 g (0.76 mol) of glycerin, 0.7 g (2.3 mmol) of bis(acetylacetonato)palladium (II), 3.0 g (5.3 mmol) of triphenylphosphine-3,3',3"-trisulfonic acid trisodium salt and 35 g of water. The mixture was heated to 80° C., whereby a water-soluble liquid phase was obtained. After cooling, 180 g (3.3 mol) of 1,3-butadiene was introduced at a time into the autoclave as a hydrocarbon solvent phase. While stirring, the mixture was heated to 80° C. again. The initial pressure in the autoclave showed 1.0 MPa. After stirring at 80° C. for 10 hours, the water phase and unreacted butadiene were removed, followed by washing with water, whereby 111 g of octadienyl glyceryl ether was obtained as a pale yellow transparent oil.

In a 500-mL autoclave were added 100 g of the resulting octadienyl glyceryl ether and 5 g of 5% Pd—C (product of NE Chemcat Corporation). The mixture was stirred at 25 to 70° C. for 6 hours under a hydrogen atmosphere of a pressure of 1 to 5 MPa. After completion of the reaction, the catalyst was filtered off, whereby 102 g of octyl glyceryl ether was obtained as a colorless transparent oil. Gas chromatography(GC) analysis showed that the monooctyl glyceryl ether content was 99%, and the dioctyl glyceryl ether content was 1% or less.

The monooctyl glyceryl ether, the product of this reaction, contained an isomer of the linear structure of formula (1a) as a main component and isomers of the branched structures of formulas (1b) and (1c) in a ratio of the linear isomer to the branched isomers of 84:16.

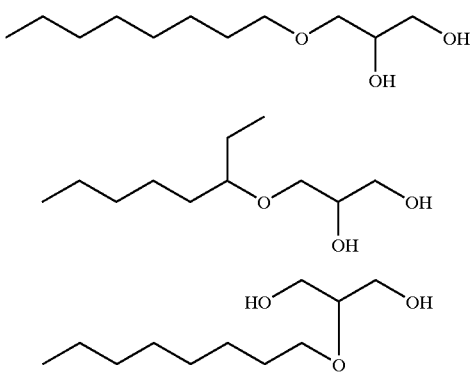

Comparative Example 1

In a 1 liter autoclave were charged 150 g (1.6 mol) of glycerin, 230 g of 2-propanol, 60 mg (0.2 mmol) of bis(acetylacetonato)palladium (II) and 103 mg (0.4 mmol) of triphenylphoshine. To the mixture, 100 g (1.85 mol) of 1,3-butadiene was introduced at a time, followed by heating to 70 C while stirring. The initial pressure in the autoclave showed 0.7 Mpa, which gradually decreased to a normal pressure after three hours. After the reaction mixture was allowed to cool to room temperature, 10 g of 5% Pd—C was added to the reaction mixture, and hydrogenation was conducted at 70° C. for 10 hours under a hydrogen atmosphere of 2 MPa. GC analysis after completion of the reaction showed that the content of monooctyl glyceryl ether in the reaction mixture was 55%, that of dioctyl glyceryl ether byproduct was 22%, and that of the glycerin remained unreacted was 14%. A ratio of the linear isomer to the branched isomers in the monooctyl glyceryl ether was found to be equivalent to that of Example 1 (linear isomer::branched isomers=84:16).

Example 2

In a 500-mL autoclave, charged were 70 g (0.76 mol) of glycerin, 0.7 g (2.3 mmol) of bis(acetylacetonato)palladium (II), 2.7 g (5.0 mmol) of triphenylphosphine-2,2'-disulfonic acid dipotassium salt dihydrate and 35 g of water. The mixture was heated to 80° C., whereby a water-soluble liquid phase was obtained. After cooling, a hydrocarbon solvent phase containing 100 g (1.85 mol) of 1,3-butadiene dissolved in 100 g of n-octane was introduced at a time into the autoclave. While stirring, the mixture was heated to 80° C. again. The initial pressure in the autoclave showed 0.9 Mpa. After stirring at 80° C. for 12 hours, the water phase and unreacted butadiene were removed. The residue was washed with water and n-octane was removed, whereby 106 g of octadienyl glyceryl ether was obtained as a pale yellow transparent oil.

In a 500-mL autoclave were added 100 g of the resulting octadienyl glyceryl ether and 5 g of 5% Pd—C (product of NE Chemcat Corporation). The mixture was stirred at 25 to 70° C. for 6 hours under a hydrogen atmosphere of 1 to 5 MPa. After completion of the reaction, the catalyst was filtered away, whereby 102 g of octyl glyceryl ether was obtained as a colorless transparent oil. GC analysis of the resulting oil showed that the content of monooctyl glyceryl ether was 99%, while that of dioctyl glyceryl ether was 1% or less.

A ratio of the linear compound to the branched compounds in the monooctyl glyceryl ether was found to be equivalent to that of Example 1 (linear isomer:branched isomer=84:16).

Example 3

In a 500-mL autoclave, charged were 70 g (0.76 mol) of glycerin, 0.9 g (3.0 mmol) of bis(acetylacetonato)palladium (II), 4.0 g (7.0 mmol) of triphenylphosphine-3,3',3"-trisulfonic acid trisodium salt and 35 g of water. The mixture was heated to 80° C., whereby a water-soluble liquid phase was obtained. After cooling to room temperature, 224 g (3.3 mol) of isoprene was added and the autoclave was purged with nitrogen. The mixture was then heated to 80° C. again. After the reaction mixture kept at 80° C. was stirred for 15 hours, the mixture was allowed to cool to room temperature. Under reduced pressure, unreacted isoprene and a small amount of dimethyloctatriene byproduct were distilled off, followed by washing with water, whereby 88 g of (dimethyloctadienyl)glyceryl ether was obtained as a yellow transparent oil.

In a 500-mL autoclave were added 50 g of the resulting (dimethyloctadienyl)glyceryl ether and 3 g of 5% Pd—C (product of NE Chemcat Corporation). The mixture was stirred at 50° C. for 12 hours under a hydrogen atmosphere of 5 MPa. After completion of the reaction, the catalyst was filtered away, whereby 49 g of mono(dimethyloctyl)glyceryl ether was obtained as a colorless transparent oil. GC analysis of the resulting oil showed that the dimethyloctyl group of the mono(dimethyloctyl)glyceryl ether was a mixture of isomers having a methyl group in the different positions, such as 3,7-dimethyl-1-octyl group and 3,6-dimethyl-1-octyl group. It was also shown that the content of the mono(dimethyloctyl)glyceryl ether was 99% and that of di(dimethyloctyl)glyceryl ether was 1% or less.

Example 4

In a 500-mL autoclave, charged were 50 g (0.37 mol) of trimethylolpropane, 0.5 g (1.6 mmol) of bis(acetylacetonato)palladium (II), 2.0 g (3.5 mmol) of triphenylphosphine-3,3',3"-trisulfonic acid trisodium salt and 50 g of water. The mixture was heated to obtain an aqueous phase. After addition of 100 g of diethylene glycol dibutyl ether, 100 g (1.85 mol) of 1,3-butadiene was introduced into the autoclave. While stirring, the mixture was heated to 80° C. again. After the mixture was stirred at 80° C. for 15 hours, an aqueous phase and unreacted butadiene were removed. The residue was washed with water, and diethylene glycol dibutyl ether was then distilled off under reduced pressure, whereby 54 g of octadienyl ether of trimethylol propane was obtained as a yellow transparent oil.

In a 500-mL autoclave were added 50 g of the resulting octadienyl ether and 2 g of 5% Pd—C (product of NE Chemcat Corporation). The mixture was stirred at 50° C. for 6 hours under a hydrogen atmosphere of 1 MPa. After completion of the reaction, the catalyst was filtered away, whereby 51 g of trimethylol propane monooctyl ether was obtained as a colorless transparent oil. GC analysis of the oil showed that the purity (content of trimethylol propane monooctyl ether) was 97%, while the content of trimethylol propane dioctyl ether was 3%.

Industrial Applicability

According to the present invention, monoalkyl glyceryl ethers can be produced selectively in a simple manner and advantageously from the economical viewpoint. In addition, the catalyst used in the present process can be recovered and recycled for reuse.

What is claimed is:

1. A process for producing a monoalkyl ether, which comprises
   a first step of contacting the following components (A) and (B):
   (A): an aqueous liquid phase containing:
      ($a_1$) a $C_{3-6}$ polyol having 3 or 4 hydroxyl groups, a palladium compound, a water-soluble tertiary phosphine or phosphite, and water; or
      ($a_2$) a $C_{3-6}$ polyol having 3 to 4 hydroxyl groups, a complex of palladium and a water-soluble tertiary phosphine or phosphite, and water, and
   (B): an oily liquid phase containing a conjugated diene to give an alkadienyl ether containing an alkadienyl group resulting from dimerization of conjugated dienes; and
      a second step of hydrogenating the alkadienyl group in the alkadienyl ether in a hydrogen atmosphere in the presence of a catalyst containing an element selected from the Groups 8 to 10 elements of the periodic table.

2. The process according to claim 1, wherein the polyol is glycerin and the oily liquid phase is a hydrocarbon solvent.

3. The process according to claim 1 or 2, wherein in the first step, the conjugated diene (B) is used as a hydrocarbon solvent.

4. The process according to claim 1, wherein the conjugated diene is 1,3-butadiene.

5. The process according to claim 1, wherein in the first step, the water-soluble tertiary phosphine or phosphite is a sulfonated aromatic tertiary phosphine or phosphite, or an alkali metal salt thereof.

6. The process according to claim 1, wherein the $C_{3-6}$ polyol is selected from the group consisting of glycerin, trimethylol methane, trimethylol ethane, trimethylol propane, and pentaerythritol.

7. The process of claim 1, wherein the $C_{3-6}$ polyol is present in an amount of 0.01 to 10 times the weight of water.

8. The process of claim 1, wherein the $C_{3-6}$ polyol is present in an amount of 0.1 to 10 times the weight of water.

9. The process of claim 1, wherein the $C_{3-6}$ polyol is present in an amount of 2 to 5 times the weight of water.

10. The process of claim 1, wherein the palladium compound is selected from the group consisting of bis(acetylacetonato)-palladium (II), palladium (II) acetate, palladium (II) chloride, and mixtures thereof.

11. The process of claim 1, wherein the palladium compound is present in an amount of 0.0001 to 0.1 moles per mole of polyol.

12. The process of claim 1, wherein the palladium compound is present in an amount of 0.001 to 0.1 moles per mole of polyol.

13. The process of claim 1, wherein the palladium compound is present in an amount of 0.001 to 0.01 moles per mole of polyol.

14. The process of claim 1, wherein the water-soluble tertiary phosphine or phosphite is a sulfonated tertiary phosphines or phosphites, or an alkali metal salt thereof.

15. The process of claim 14, wherein the sulfonated tertiary phosphine or phosphite, or alkali metal salt thereof, is selected from the group consisting of mono-, di-, or tri-sulfonated aliphatic phosphines or phosphites; mono-, di-, or tri-sulfonated aromatic phosphines or phosphites; and mono-, di-, tri- or higher sulfonated aromatic-aliphatic phosphines or phosphites.

16. The process of claim 1, wherein the water-soluble tertiary phosphine or phosphite is present in an amount of 0.1 to 4 moles per mole of palladium compound.

17. The process of claim 1, wherein the water-soluble tertiary phosphine or phosphite is present in an amount of 1 to 4 moles per mole of palladium compound.

18. The process of claim 1, wherein the conjugated diene is selected from the group consisting of 1,3-alkadienes, 2,4-alkadienes, alkadienes having 4–6 carbon atoms, 1,3-butadiene, 1,3-pentadiene, 1,3-hexadiene, and isoprene.

19. The process of claim 1, wherein the oily liquid phase further comprises a solvent which can dissolve the conjugated diene and the monoalkylether, and which is immiscible with the aqueous liquid phase.

20. The process of claim 19, wherein the solvent is a hydrocarbon solvent selected from the group consisting of $C_{6-20}$ saturated aliphatic hydrocarbons, hexane, heptane, octane, nonane, decane, undecane, dodecane, tridecane, tetradecane, pentadecane, hexadecane, heptadecane, octadecane, nonadecane, and icosane.

21. The process of claim 19, wherein the solvent is a glycol diether selected from the group consisting of ethyleneglycol dialkyl ethers, diethylene glycol dialkyl ethers, ethyleneglycol dibutyl ether, ethyleneglycol butyl methyl ether, ethyleneglycol butyl ethyl ether, and diethyleneglycol dibutyl ether.

22. The process of claim 1, wherein the conjugated diene is present in an amount of from 1.0 to 10.0 moles per mole of polyol.

23. The process of claim 1, wherein the conjugated diene is present in an amount of 1.0 to 6.0 moles per mole of polyol.

* * * * *